Figure 1:
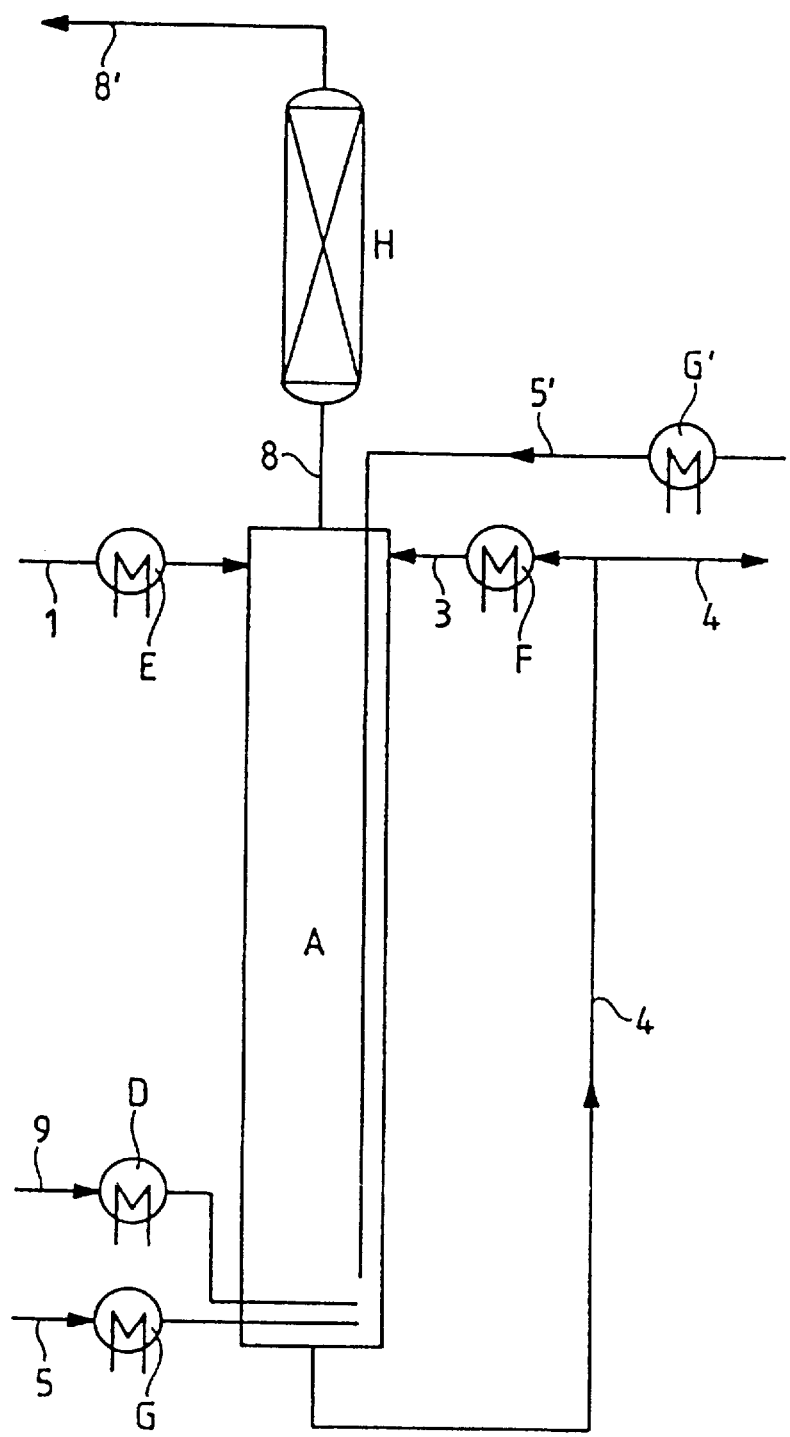

United States Patent [19]

Buysch et al.

[11] Patent Number: 5,821,377
[45] Date of Patent: Oct. 13, 1998

[54] PROCESS FOR THE CONTINUOUS PRODUCTION OF DIARYL CARBONATES

[75] Inventors: Hans-Josef Buysch; Carsten Hesse, both of Krefeld; Johann Rechner, Kempen, all of Germany

[73] Assignee: Bayer Aktiengesellschaft, Germany

[21] Appl. No.: 825,603

[22] Filed: Apr. 1, 1997

[30] Foreign Application Priority Data

Apr. 9, 1996 [DE] Germany ................ 196 14 062.5

[51] Int. Cl.$^6$ ................................................. C07C 68/00
[52] U.S. Cl. ..................... 558/274; 558/271; 558/272; 558/273
[58] Field of Search ............................................. 558/274

[56] References Cited

U.S. PATENT DOCUMENTS

| | | | |
|---|---|---|---|
| 4,201,721 | 5/1980 | Hallgren | 558/274 X |
| 5,142,086 | 8/1992 | King, Jr. et al. | 558/274 |
| 5,231,210 | 7/1993 | Joyce et al. | 558/274 |
| 5,336,803 | 8/1994 | Kezuka et al. | 558/274 X |
| 5,380,907 | 1/1995 | Mitzukami et al. | 558/274 X |
| 5,543,547 | 8/1996 | Iwane et al. | 558/274 |

FOREIGN PATENT DOCUMENTS

| | | |
|---|---|---|
| 0 614 876 | 9/1994 | European Pat. Off. . |
| 736 325 | 10/1996 | European Pat. Off. . |
| 2815512 | 10/1979 | Germany . |
| 4/257 546 | 9/1992 | Japan . |
| 4/261 142 | 9/1992 | Japan . |

OTHER PUBLICATIONS

Database CAPLUS on STN®, Chemical Abstracts Service, (Columbus, Ohio), No. 1980:163723; Hallgren, J.E., DE 2 815 512, Oct. 18, 1979, abstract, 1980.

Primary Examiner—Michael G. Ambrose
Attorney, Agent, or Firm—Connolly & Hutz

[57] ABSTRACT

In the process for the production of diaryl carbonates by oxidative carbonylation of the underlying aromatic hydroxy compounds in the presence of a catalyst containing a platinum group metal, a co-catalyst, a quaternary salt and a base, the catalyst is used as a supported catalyst in a stationary arrangement or in the fluid phase and the reaction is performed in the condensed phase. The co-catalyst is preferably also attached to the support.

9 Claims, 3 Drawing Sheets

PROCESS FOR THE CONTINUOUS PRODUCTION OF DIARYL CARBONATES

The present invention relates to a process for the production of diaryl carbonates by reacting an aromatic hydroxy compound, for example phenol, with carbon monoxide and oxygen in the presence of a catalyst, a co-catalyst, a quaternary salt and a base, in which a supported catalyst in a stationary arrangement or in the fluid phase is used for the reaction and the reaction is performed in the condensed phase, the water of reaction is continuously stripped out with reaction gas, the reaction solution is continuously discharged, the diaryl carbonate formed is separated from the reaction solution by extraction, crystallisation or distillation, is worked up without loss by crystallisation or distillation to yield high purity diaryl carbonate and the remaining reaction solution is returned to the reactor.

It is known to produce organic carbonates by the oxidative reaction of aromatic hydroxy compounds with carbon monoxide in the presence of a homogeneous noble metal catalyst (DE-OS 28 15 512). The noble metal used is preferably palladium. A co-catalyst, for example salts of manganese or cobalt, a base, a quaternary salt, various quinones or hydroquinones and desiccants may also be used. The reaction may be performed in a solvent, preferably methylene chloride. However, scaling this reaction up to an industrial process is difficult due to the use of a homogeneous noble metal catalyst, which must be recovered in a complicated manner, as the noble metal is a significant cost factor. Any losses of noble metal catalyst must be compensated at high cost and, moreover, no residues of the noble metal catalyst may remain in the product. However, an economic and efficient recovery system for catalyst systems which are used for oxidative carbonylation of aromatic hydroxy compounds to yield diaryl carbonates has not hitherto become known.

JP 04/257 546 and JP 04/261 142 each describe in one example a supported catalyst, in which silicon carbide pellets are used as a material for a supported catalyst in a distillation column. Although severe conditions (elevated pressure, elevated temperature) are used in the examples concerned, this catalyst allows only very low space/time yields, so making economic production of aromatic carbonates with such supported catalysts impossible. JP 04/257 546 also describes continuous removal of water of reaction by distillation in the distillation column; the remaining reaction products are discharged together with the noble metal catalyst in the distillation bottoms. A disadvantage of this process is that, in order to remove the water of reaction, the reaction must be performed in a distillation column, the design of which allows only short residence times and which is suitable only for removing volatile components. The person skilled in the art also knows that the solubility of gases, in this case the $CO/O_2$ reaction gas, is greatly reduced under distillation conditions. A distillation column operated in the conventional manner has a steep temperature gradient along its vertical axis with very high bottom temperatures being required to maintain this gradient. Under these conditions, the catalyst system accumulating in the bottoms undergoes considerable damage, which results in catalyst losses, decomposition of diaryl carbonate and further secondary reactions. The space/time yields achievable with this process of only 17.8 g/l×h are consequently very low. Distillation columns are thus not suitable as reactors for the oxidative carbonylation of aromatic hydroxy compounds to yield diaryl carbonates. Another disadvantage is the extremely high catalyst costs required for these space/time yields. Thus, in Example 1 of JP 04/257 546, a total of 3 g/h of palladium compound and 14.4 g/h of quaternary ammonium salts are used at a loading of 182 g of phenol per hour. At a stated yield of 35 g of diphenyl carbonate per hour, only 16.3 catalyst cycles are achieved in 1 hour. This means that at least 30 g of pure palladium (corresponding to approximately 90 g of palladium compound) are required to produce 1 kilogram of diphenyl carbonate using this process. This entails very high capital costs for the catalyst. The problem of separating and recovering the noble metal catalyst from the reaction products has not been solved, so making it impossible to exploit the reaction economically. The use of large quantities of halides at elevated temperatures of 150° to 180° C., as are required in this process, results in major corrosion problems, which entail elevated plant and equipment costs. The person skilled in the art also knows that under the stated reaction conditions, the iodide of the quaternary salts, which is preferably used as the salt, is not stable and is to a great extent oxidized to iodine. This results in considerable losses of the quaternary salt and in the formation of secondary products, which further severely impairs the selectivity and thus the economic viability of this process. JP 04/261 142 describes a process which is operated in the same manner as in JP 04/257 546, but with the difference that additional reactors are connected to the distillation column in order to increase residence times. The above-stated problems of corrosion, catalyst costs and loss of quaternary salt and the associated secondary reactions are not solved in this application. The proposed apparatus is also no more advantageous, as all the disadvantages arising from the use of distillation columns as reactors still occur. While residence time is indeed increased by the additional reactors, the proposed design results in considerable back-mixing within the apparatus, such that secondary reactions may proceed to a greater extent, so reducing selectivity. Thus, in practical example 1 of JP 04/261 142, a selectivity of only 97% is achieved, in comparison with 99% in the corresponding Example 1 of JP 04/257 546. At approximately 9 g/l×h, the space/time yields achievable with this process are still lower than in JP 04/257 546. The additional reactors make effective removal of the water of the reaction impossible. Indeed, in the proposed process, the water of reaction formed in the reactors during the reaction is removed only subsequently in the distillation column. Under the reaction conditions, the carbonate formed in the reactors is hydrolytically cleaved again, as a result of which only very low levels of conversion are achievable.

No process for the production of diaryl carbonates by reacting an aromatic hydroxy compound with carbon monoxide and oxygen has thus hitherto become known which allows performance of the process in an economic, continuous manner at an elevated space/time yield without damaging the catalyst. The object thus arose of providing a process having elevated activity and selectivity, which allows the economic, continuous production of diaryl carbonates by reacting an aromatic hydroxy compound with carbon monoxide and oxygen without damaging the catalyst.

It has now surprisingly been found that the stated disadvantages may be overcome if the reaction is performed in the condensed phase in the presence of a supported catalyst in a stationary arrangement or in the fluid phase, the reaction solution is continuously discharged from the reactor, the diaryl carbonate formed is separated from the reaction solution by crystallisation, distillation or extraction, is worked up largely without loss by further crystallisation or distillation to yield high purity diaryl carbonate and the remaining reaction solution is returned to the reactor.

The present invention accordingly provides a process for the continuous production of diaryl carbonates of the formula $$R^1\text{—O—CO—O—}R^1 \qquad (I)$$

by reacting aromatic hydroxy compounds of the formula $$R^1\text{—OH} \qquad (II),$$

wherein in the formulae

R$^1$ means unsubstituted or substituted C$_6$–C$_{15}$ aryl, preferably unsubstituted or substituted phenyl, particularly preferably unsubstituted phenyl, with carbon monoxide and oxygen at 30°–200° C., preferably at 30°–150° C., particularly preferably at 40°–120° C., and at 1–120 bar, preferably at 2–80 bar, particularly preferably at 5–25 bar, in the presence of a platinum group metal or a compound of a platinum group metal as the catalyst, a co-catalyst, a quaternary salt and a base, which process is characterised in that the catalyst is used as a supported catalyst in a stationary arrangement or in the fluid phase and the reaction is performed in the condensed phase.

The process according to the invention may be represented by the following formula, taking the formation of diphenyl carbonate by way of example:

$$2C_6H_5\text{—OH} + CO + \tfrac{1}{2}O_2 \rightarrow (C_6H_5O)_2CO + H_2O.$$

Aromatic hydroxy compounds which may be used according to the invention and on which the diaryl carbonates are based are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol, o-, m-, p-phenylphenol and bisphenol A, preferably phenol. Where the aromatic hydroxy compound is substituted, it generally has 1 or 2 substituents with the meaning C$_1$–C$_4$ alkyl, C$_1$–C$_4$ alkoxy, fluorine, chlorine or bromine or the residue HO—C$_6$H$_4$—C(CH$_3$)$_2$—.

When in the reactive state, the supported catalysts usable in the process according to the invention contain a platinum group metal or a compound of a platinum group metal, preferably a platinum group metal halide or a complex compound containing a platinum group metal halide or a compound which may be converted under reaction conditions into a platinum group metal, a platinum group metal halide or a complex compound containing a platinum group metal halide, in a quantity of 0.01 to 15 wt. %, preferably of 0.05 to 10 wt. %, calculated as the platinum group metal and relative to the entire weight of the catalyst. Platinum group metals which may be considered are Pt, Ir, Pd, Ru or Rh or two or more thereof. Pd and Rh or a mixture thereof are, however, preferred, in particular Pd. The catalyst may also contain a co-catalytically active metal compound from groups IB, IIB, IIIA, IVA, IVB, VB, VIB, VIIB, from the iron group (atomic numbers 26–28) or from the rare earth metals (atomic numbers 58–71) of Mendeleyev's periodic system of the elements in a quantity of 0.01 to 15 wt. %, preferably of 0.05 to 10 wt. %, calculated as metal and relative to the entire weight of the catalyst. Such catalysts are present as a completely heterogeneous catalytic system, so avoiding mixing and contamination of the reaction product with catalyst fractions.

Suitable catalyst supports are any industrially conventional catalyst supports based on carbon, element oxides, element carbides or element salts in various presentations. Examples of supports containing carbon are coke, graphite, carbon black or activated carbon. Examples of element oxide catalyst supports are SiO$_2$ (natural or synthetic silicas, quartz), Al$_2$O$_3$ (α-, γ-Al$_2$O$_3$), aluminas, natural and synthetic aluminosilicates (zeolites), TiO$_2$ (rutile, anatase), ZrO$_2$ or ZnO. Examples of element carbides and salts are, inter alia, SiC, AlPO$_4$, BaSO$_4$, CaCO$_3$. They may be used both as chemically uniform pure substances and as a mixture. Materials in both agglomerated and powder form are suitable for use according to the invention as catalyst supports. Where the supported catalyst is arranged as a fixed bed, the support is preferably used as moulded shapes, for example in the form of spheres, cylinders, rods, hollow cylinders, rings etc.. Catalyst supports may optionally be further modified by extrusion, tabletting, optionally with the addition of further catalyst supports or binders, such as SiO$_2$ or Al$_2$O$_3$, and calcination. The preparation and further processing of the catalyst supports used according to the invention are well known to the person skilled in the art. Noble metals may be applied using known methods, for example by impregnation, precipitation or adsorption.

In the event that the supported catalyst does not already contain a co-catalyst, a co-catalyst is added to the reaction solution. The co-catalyst is a metal compound of the above-stated groups IB, IIB, IIIA, IVA, IVB, VB, VIB, VIIB, of the iron group (atomic numbers 26–28) or of the rare earth metals (atomic numbers 58–71) of Mendeleyev's periodic system of the elements, wherein the metal may be used in various oxidation states. Without restricting the process according to the invention Mn, Cu, Co, V, Zn, Ce and Mo may be cited as preferred, with Mn, Co, Cu, Mo and Ce being particularly preferred. The metal may be used, for example, as halides, oxides, carboxylates of C$_2$–C$_6$ carboxylic acids, diketonates or nitrates and as complex compounds, which may for example contain carbon monoxide, olefins, amines, nitriles, phosphines and halides. Manganese(II) compounds are preferably used in the process according to the invention, particularly preferably manganese(II) complexes, very particular preferably manganese(II) acetylacetonate. The co-catalyst is used in a quantity such that its concentration in the complete reaction mixture is 0 to 20 wt. %, preferably 0 to 5 wt. %, particularly preferably 0 to 2 wt. %. The lower limit 0 (zero) here describes the case in which the co-catalyst is attached in the above-stated manner to the catalyst support.

Suitable quaternary salts for use in the process according to the invention are ammonium and phosphonium salts, which bear identical or different C$_6$ to C$_{10}$ aryl, C$_7$ to C$_{12}$ aralkyl and/or C$_1$ to C$_{20}$ alkyl residues as organic residues and a halide, tetrafluoroborate or hexafluorophosphate as an anion or a mixture of two or more thereof. Ammonium salts containing C$_6$ to C$_{10}$ aryl, C$_7$ to C$_{12}$ aralkyl and/or C$_1$ to C$_{20}$ alkyl residues as the organic residues and a halide as an anion are preferred, with tetrabutylammonium bromide being particularly preferred. The quantity of such a quaternary salt is 0.1 to 50 wt. %, relative to the weight of the reaction mixture. This quantity is preferably 0.5 to 15 wt. %, particularly preferably 1 to 5 wt. %.

Any desired bases or mixtures thereof, whether organic or inorganic may be used in the process according to the invention. Examples of inorganic bases which may be cited without restricting the process according to the invention are alkali metal hydroxides and carbonates, C$_2$–C$_{12}$ carboxylates or other salts of weak acids, together with alkali metal salts of aromatic hydroxy compounds of the formula (II), for example alkali metal phenolates. The hydrates of alkali metal phenolates may, of course, also be used in the process according to the invention. An example of such a hydrate which may be cited without restricting the process according to the invention is sodium phenolate trihydrate. The quantity of water added is, however, preferably calculated such that at most 5 mol of water are used per mol of base. Higher concentrations of water generally result in poorer conversion and decomposition of the carbonates formed. Organic bases which may be cited without restricting the process according to the invention are tertiary amines, which may bear identical or different $C_6$ to $C_{10}$ aryl, $C_7$ to $C_{12}$ aralkyl and/or $C_1$ to $C_{20}$ alkyl residues as organic residues, together with pyridine bases or hydrogenated pyridine bases, for example triethylamine, tripropylamine, tributylamine, trioctylamine, benzyldimethylamine, benzyldimethylamine, dioctylbenzylamine, dimethylphenylethylamine, 1-dimethylamino-2-phenylpropane, pyridine, N-methylpiperidine, 1,2,2,6,6-pentamethylpiperidine. Preferably, the base used is an alkali metal salt of the aromatic hydroxy compound, particularly preferably an alkali metal salt of the aromatic hydroxy compound which is also to be reacted to yield the organic carbonate. These alkali metal salts may be lithium, sodium, potassium, rubidium or caesium salts. Lithium, sodium and potassium phenolate are preferably used, particularly preferably sodium phenolate. The quantity of base is 0.01 to 20 wt. %, relative to the weight of the reaction mixture. This quantity is preferably 0.05 to 15 wt. %, particularly preferably 0.1 to 5 wt. %.

The base may be added to the reaction mixture as a pure compound in solid form or as a melt. In another embodiment of the invention, the base is added to the reaction mixture as a solution, which contains 0.1 to 80 wt. %, preferably 0.5 to 65 wt. %, particularly preferably 1 to 50 wt. % of the base. The solvent used in this case may be both alcohols or phenols, such as for example the phenol to be reacted, and inert solvents. Examples of solvents which may be cited are dimethylacetamide, N-methylpyrrolidinone, dioxane, t.-butanol, cumyl alcohol, isoamyl alcohol, tetramethylurea, diethylene glycol, halogenated hydrocarbons (for example chlorobenzene or dichlorobenzene) and ethers. These solvents may be used alone or in any desired combination with each other. One embodiment of the invention thus consists in dissolving the base in a phenol melt, which has been diluted with a solvent. The base is preferably dissolved in the melt of an aromatic hydroxy compound, particularly preferably in a melt of the aromatic hydroxy compound which is to be reacted to yield the organic carbonate. The base is very particularly preferably added dissolved in phenol; this preferably means dispensing with further solvents of the stated type.

The process according to the invention is performed at 30° to 200° C., preferably at 30° to 150° C., particularly preferably at 40° to 120° C. and at a pressure of 1 to 120 bar, preferably of 2 to 80 bar, particularly preferably of 5 to 25 bar.

The process according to the invention is preferably performed without solvent, i.e. solely in the melt of the aromatic hydroxy compound to be reacted. Inert solvents of the type cited above by way of example for dissolving the base, may, of course, also be used.

The reaction gas for the process according to the invention consists of carbon monoxide (CO) and oxygen ($O_2$). An inert gas may additionally be present. The reaction gas is introduced in a quantity of 1 to 100000 Nl per liter of reaction solution, preferably of 5 to 50000 Nl per liter of reaction solution and particularly preferably of 10 to 10000 Nl per liter of reaction solution.

The composition of the constituents CO and O2 may be varied within wide concentration limits, but a CO:$O_2$ molar ratio (standardised to CO) of 1:(0.001–1.0), preferably of 1:(0.01–0.5) and particularly preferably of 1:(0.02–0.3) is conveniently established. At these molar ratios, the $O_2$ partial pressure is high enough for elevated space/time yields to be achieved without entailing the danger of forming explosive $CO/O_2$ gas mixtures. The constituents are not subject to any particular purity requirements, it thus being possible to use synthesis gas as the source of CO and air as the source of $O_2$, but care must be taken to ensure that no catalyst poisons, such as for example sulphur or compounds thereof, are introduced. In the preferred embodiment of the process according to the invention, pure CO and pure $O_2$ are used. In another preferred embodiment of the process according to the invention, CO and $O_2$ are mutually independently apportioned. The $O_2$ may optionally in this case be apportioned together with inert gas. Where a series of reactors is used instead of a single reactor, $O_2$ is preferably separately apportioned in such a manner that the optimum $O_2$ concentration is ensured in each of the reactors. Inert constituents of the reaction gases in the process according to the invention may be nitrogen, hydrogen, noble gases and organic compounds stable under the reaction conditions, which preferably form an azeotrope with water. The concentration of inert gas in the reaction gas may be 0 to 30 vol. %, preferably 0 to 15 vol. % particularly preferably 0 to 5 vol. %. The concentration 0 vol. % represents the special case of the preferred state without inert gas.

By means of a separating unit located in the waste gas stream, for example a dephlegmator, distillation columns with plates or packing and other apparatuses known to the person skilled in the art, the greatest part of the entrained phenol or solvent may be returned to the reactor. In the preferred embodiment, the excess reaction gas enriched with water may, after separation of the water, be returned to the reactor. Water is separated from the reaction gas using known means, for example by adsorption, absorption or preferably by cooling the pressurised gas and condensing the water (*Ullmann's Encyclopedia of Industrial Chemistry*, 5th edition, volume A5, pages 203 et seq., Weinheim 1986; *Ullmann's Encyclopedia of Industrial Chemistry*, 5th edition, volume A12, pages 169 et seq., 1989).

Reactors which may be considered for the process according to the invention are those in which, in contrast with distillation columns, all the reactants, with the exception of the permanent gases CO and $O_2$, are present in the condensed phase.

The catalyst may be in a stationary arrangement or may be in the fluid phase. Examples of such reactors for catalysts present in the fluid phase are stirred tanks, fluidised bed reactors and bubble columns, wherein these may be used as individual reactors or as a series of reactors. A series of reactors may comprise 2 to 15, preferably 2 to 10, particularly preferably 2 to 5 reactors connected in series.

If the supported catalyst is used as a powder (for the fluid phase), the stirred vessels to be used are equipped, in order to mix the reaction components, with stirrers suitable for this purpose; in bubble columns and fluidised bed reactors, the reaction mixture is mixed by the gases CO and $O_2$. When using supported catalyst powders as a suspension in stirred vessels or bubble columns, quantities of 0.001 to 50 wt. %, preferably from 0.01 to 20 wt. %, particularly preferably from 0.1 to 10 wt. %, of the supported catalyst powder are used, relative to the introduced quantity of aromatic hydroxy compound.

Suspended catalysts may be separated from the reaction mixture by, for example, filtration, settling or centrifugation and returned to the reactor. Liquid fractions of the reaction mixture may, of course, also be discharged from the reactor through a sintered filter, wherein the catalyst remains in the reactor.

In preferred embodiments, the heterogeneous supported catalyst is used as a stationary arrangement in stirred tanks, bubble columns, fixed bed reactors, trickle-bed reactors or series of these reactors, wherein the different types of reactors may also simultaneously be present in a series of reactors; such reactors are described in *Ullmann's Encyclopedia of Industrial Chemistry*, 5th edition 1989, volume B4, part B, pages 98 et seq.. In the case of continuous operation, wherein the gas and fluid phase may be passed counter- or co-currently, and in the trickle phase on a fixed bed catalyst, loadings of 0.01 to 20 g, preferably 0.05 to 10 g, particularly preferably of 0.1 to 5 g of aromatic hydroxy compound per gram of supported catalyst per hour. Supported catalysts in a stationary arrangement may remain in the reactor for an extended period. Bubble columns and similar reactors which may be used in the process according to the invention are of the following types: simple bubble columns, bubble columns with inserts, such as for example bubble columns with parallel chambers, bubble columns connected in series with screen plates or single-hole plates, bubble columns with packings, with static mixers, pulsed screen plate bubble columns; loop reactors, such as for example giant loop reactors, downflow loop reactors, jet loop reactors, free-jet loop reactors, jet nozzle reactors; bubble columns with immersed fluid spargers, downflow/upflow bubble columns and other bubble column reactors known to the person skilled in the art (H. Gerstenberg, *Chem. Ing. Tech.* 61 (1979), no. 3, pages 208–216; W.-D. Deckwer, *Reaktionstechnik in Blasensdulen*, Otto Salle Verlag, 1985). In the preferred embodiment, bubble column reactors and bubble columns connected in series are used which allow effect mixing of the gas and fluid phase, such as for example bubble columns connected in series and loop reactors. In order to maintain thorough mixing of liquid and reaction gas, distributing and redispersion devices may be located along the longitudinal axis of the bubble column reactors. Fixed redispersion devices which are used are single-hole plates, perforated plates, screen plates and other inserts known to the person skilled in the art. Such reactors are known and are described, for example, in *Catal.Rev.-Sci.-Eng.* (1995), volume 37(2), pages 227–309. Initial dispersion of the reaction gas in the liquid phase on addition may be achieved with conventional devices such as porous sintered plates, perforated plates, screen plates, injection tubes, nozzles, gas dispersion rings and further dispersion devices known to the person skilled in the art.

Figure 2:
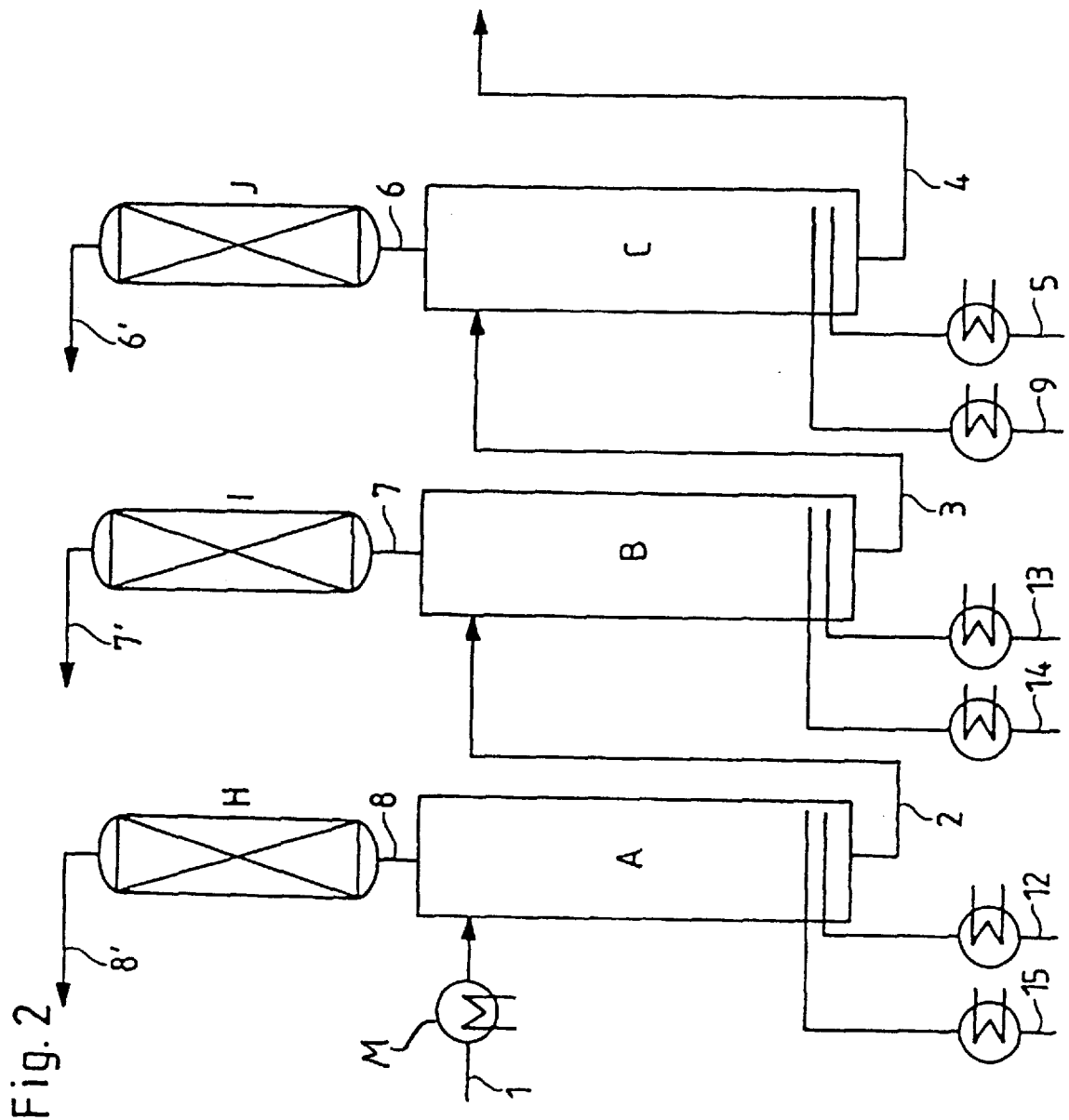
Figure 3:
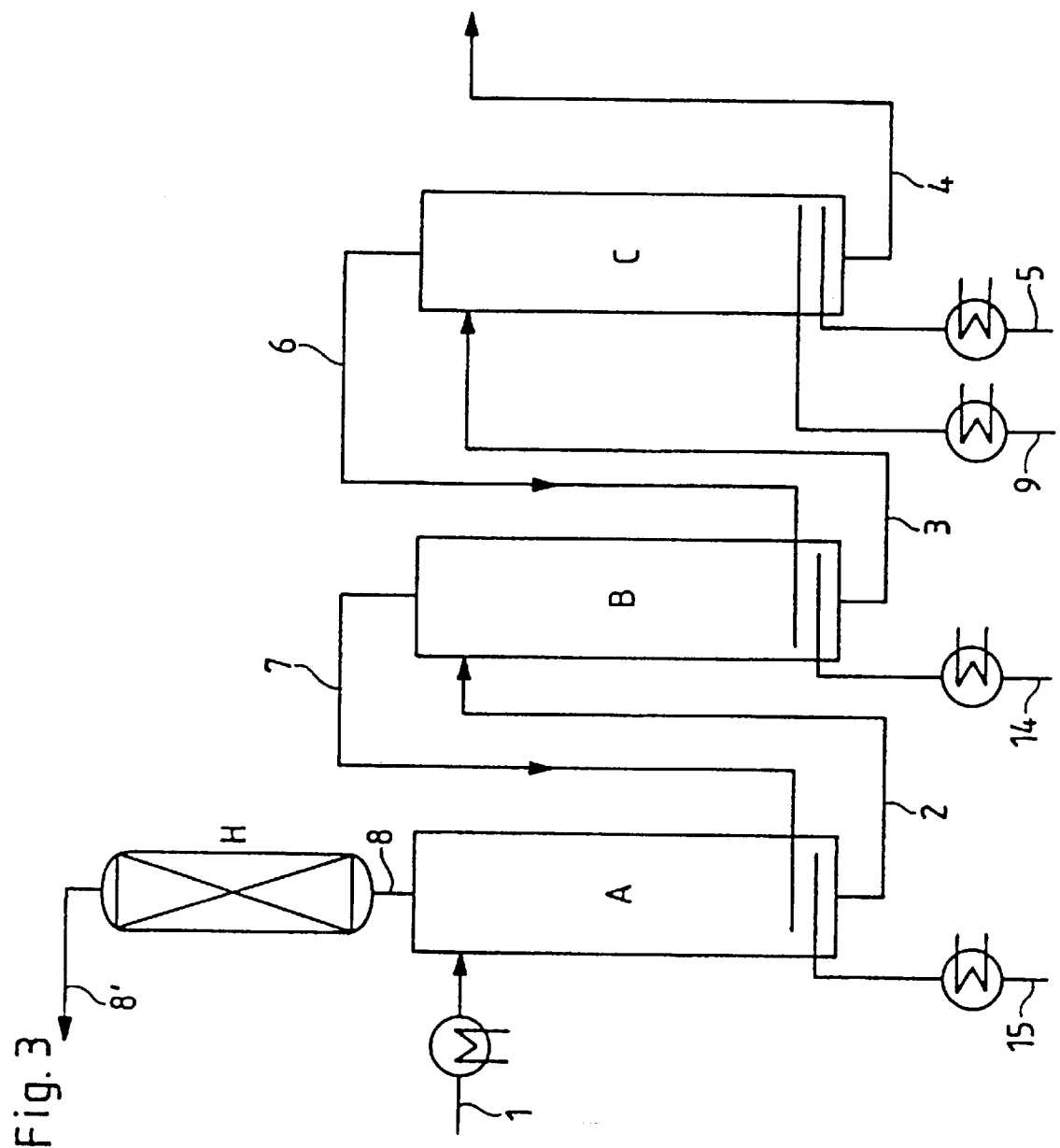

In the preferred embodiment of the process according to the invention, the process is operated continuously in a single reactor or in a series of reactors. FIGS. 1, 2 and 3 show example modes of operation with one or three reactors (A, B and C), wherein the mode of operation according to the invention should not be restricted to these examples.

One example embodiment of the process according to the invention involves continuously adding the solution of the components of the reaction system (aromatic hydroxy compound, base, quaternary salt and optionally co-catalyst) in the above-stated concentrations via line (1), FIG. 1, into the reactor (A). The liquid reaction components may optionally be heated to the intended reaction temperature by means of an upstream heating unit (E). The liquid phase to be discharged from (A) is discharged from the lower end of the reactor and passed via line (4) for working up. The desired filling level in the continuously operated reactor is controlled using known methods. A partial stream may optionally be returned via line (3) to (A). The liquid reaction components may optionally be reheated to the intended reaction temperature by means of an upstream heating unit (F). The reaction gas consisting of CO and $O_2$ may be introduced via line (5) or (5') into the lower end of (A) and optionally previously preheated to the reaction temperature by a preheater (G) or (G'). $O_2$ may here be apportioned independently from CO and inert gas, or apportioned together with inert gas. Where $O_2$ is separately apportioned, it passes through line (9) and preheater (D). CO and $O_2$ are here distributed in the reaction mixture in the above-stated quantities either, in the case of a stirred tank, through a sparging agitator or by other gas distribution units. The excess reaction gas leaves the reactor together with the water of reaction and entrained educt (II) via line (8). The greatest part of the educt (II) is separated in the separator (H) and returned to the reactor (A). Excess reaction gas together with the water of reaction leaves the reactor via line (8'). The water of reaction is removed from the reaction gas in a known manner. The reaction gas is then reintroduced into the reactor (A) together with the replacement for the consumed reaction gas.

Where a series of reactors is used (FIGS. 2 and 3), the above-stated liquid reaction components are apportioned into the first reactor (A) and may optionally be preheated to the intended reaction temperature in an upstream heating unit (M). They are preferably introduced into the upper end of the reactor in liquid form via line (1).

The liquid phase to be discharged from each reactor is discharged at the lower end of the reactor and is reintroduced via lines (2) and (3) respectively into the upper end of the next reactor (B) or (C). The product stream is discharged via line (4) and passed for working up. The desired filling level in the continuously operated reactors is controlled using known methods. Where a series of reactors is used, the gas phase may be passed through the continuously running stream of liquid either crosscurrently (FIG. 2) or countercurrently (FIG. 3). Crosscurrently means in this connection that the reaction gases are apportioned via lines (12), (13) and (5) (FIG. 2) and are each again discharged together with the water of reaction and entrained educt (II) at the upper end of each reactor via lines (8), (7) and (6) (FIG. 2), i.e. the reaction gas passes through the reactors transversely relative to the direction of flow of the liquid phase. Where $O_2$ is separately apportioned, it passes through lines (9), (14) and (15). The educt (II) is separated in the separators (H), (I) and (J) and returned to the appropriate reactors. Excess reaction gas together with the water of reaction leaves the reactor via lines (8'), (7') and (6'). Once the waste gas streams have been combined, the water of reaction is removed from the reaction gas in a known manner. The reaction gas is then reintroduced into the reactors (A), (B) and (C) together with the replacement for the consumed reaction gas. The total quantity of apportioned reaction gas may be distributed at will among the individual reactors. Each individual reactor is preferably operated with the liquid phase and gas phase flowing countercurrently.

Countercurrent operation (FIG. 3) means that the reaction gases are apportioned via line (5) into the final reactor (reactor C in FIG. 3), are continuously passed via lines (6) and (7) against the flow of the liquid phase running from the first reactor (A) to the last reactor (C) in FIG. 3 and are reintroduced at the lower end of the following reactor (B) and (A). Where $O_2$ is separately apportioned, it passes through lines (9), (14) and (15). The liquid phase is apportioned and passed through the reactors in the same manner as in crosscurrent operation. The excess reaction gas together with the water of reaction and entrained educt (II) is discharged at the upper end of the first reactor (A in FIG. 3) via line (8). The greatest part of the educt (II) is separated in the separator (H) and returned to the reactor (A). Excess reaction gas together with the water of reaction leaves the reactor via line (8'). The water of reaction is removed from the reaction gas in a known manner and the reaction gas is then reintroduced into the reactor (C) together with the replacement for the consumed reaction gas.

The liquid reaction mixture may be worked up, for example, by distillation, crystallisation or extraction. In the case of working up by distillation, the unreacted aromatic hydroxy compound is first separated. In a further stage, the aromatic carbonate is isolated. The catalyst components remaining in the residue (quaternary salt, base, optionally co-catalyst) may be recovered and recycled. In the case of working up by crystallisation, the reaction solution is discharged from the reactor, cooled and seeded in an appropriate manner. In a first stage, a crystallisate is separated which consists of a mixture of diaryl carbonate and aromatic hydroxy compound. This may be achieved, for example, by fractionated melt crystallisation in a tubular crystalliser or by suspension crystallisation, for example in a stirred tank. In the case of fractionated melt distillation, secondary products and residues of the reaction system (quaternary salt, base, optionally co-catalyst) are separated from the crystallisate by exudation and returned together with the melt to the reactor. In the case of suspension crystallisation, secondary products and residues of the reaction system (quaternary salt, base, optionally co-catalyst) are washed out of the crystallisate with an anhydrous washing solution, preferably a mixture of diaryl carbonate and aromatic hydroxy compound. The melt and washing solution may then be returned to the reactor without further treatment. The crystallisates purified in this manner, which consist of a mixture of diaryl carbonate and aromatic hydroxy compounds, are worked up without loss into high purity diaryl carbonate by crystallisation or distillation and the aromatic hydroxy compound arising from this working up is returned to the reactor.

In the case of working up by extraction, the reaction solution is discharged from the reactor, vigorously mixed with a selective extracting agent and the phases are then separated. The resultant extracted phase is depleted in aromatic carbonate and aromatic hydroxy compound and may still contain, in addition to the homogeneous reaction components (quaternary salt, base, optionally co-catalyst), a few percent of dissolved extractant. These fractions of dissolved extractant may be separated, for example, by distillation and returned to the extraction stage. The depleted extracted phase is then returned to the reactor. The clear extractant phases contain, in addition to the extracting agent, only the aromatic hydroxy compound, the aromatic carbonate together with slight traces of the catalyst system. Once the extractant has been separated (for example by distillation) and returned to the extraction stage, the residue is worked up into high purity diaryl carbonate by crystallisation or distillation and the aromatic hydroxy compound arising from this working up is returned to the reactor.

EXAMPLES

Example 1

Production of a pulverulent supported catalyst:

a) Surface-modification of a titanium dioxide powder with palladium and manganese:

300 ml of a solution of 40.5 g (0.16 mol) of manganese(II) nitrate 4 hydrate in water were added to a slurry of 283.5 g of titanium dioxide powder (Norton) in 1500 ml of water. An alkaline pH was then established with dilute sodium hydroxide solution. The suspension was suction filtered, washed with water, dried at 100° C. and heat treated for 3 hours at 300° C. A slurry of the manganese-doped support was prepared in 1500 ml of water and combined with 300 ml of solution containing 50 g of sodium tetrachloropalladate(II) solution containing 15% palladium. An alkaline pH was then established with dilute sodium hydroxide solution. The suspension was suction filtered, washed and dried at 100° C. The catalyst contained 2.5% of Pd and 3% of Mn, each calculated as metal.

b) Surface-modification of a titanium dioxide powder with palladium and cobalt:

283.5 g of titanium dioxide powder (Norton) were added to a solution of 18.75 g of palladium(II) bromide (0.07 mol), 28.5 g of sodium bromide (0.28 mol) and 33.4 g of cobalt(II) bromide (0.15 mol) in 1500 ml of water. An alkaline pH was then established with dilute sodium hydroxide solution. The suspension was suction filtered, washed and dried at 100° C. The catalyst contained 2.5% of Pd and 3% of Co, each calculated as metal.

c) Surface-modification of cerium dioxide powder with palladium:

25 g of cerium dioxide powder (Strem) were added to a solution of 2.28 g (2.5 mmol) of bis(tetrabutylammonium) tetrabromopalladate in 500 ml of reagent-grade dichloromethane. The mixture was then stirred for 5 hours and suction filtered. The resultant supported catalyst was dried for 17 hours at 50° C. under a vacuum (30 mbar). Determination of palladium content by atomic absorption spectrometry revealed that the supported catalyst contained 1.0 wt. % of palladium (calculated as metal).

d) Surface-modification of manganese oxide powder with palladium:

300 ml of solution of 50 g of sodium tetrachloropalladate (II) solution containing 15% palladium in water were added at room temperature to a slurry of 292.5 g of manganese dioxide powder in 1500 ml of water. An alkaline pH was then established with dilute sodium hydroxide solution. The suspension was suction filtered and dried at 100° C. The heterogeneous catalyst contained 2.5% of Pd on an $MnO_2$ support, calculated as metal.

Example 2

Production of agglomerated supported catalyst:

a) Surface-modification of a titanium dioxide extrudate with palladium and manganese:

200 ml of titanium dioxide extrudate were impregnated with 58.4 ml of solution of 21.6 g of manganese(1I) chloride in water. Drying was then performed under nitrogen at 110° C. The manganese-doped support was impregnated with 58 ml of solution containing 33.3 g of sodium tetrachloropalladate(II) solution containing 15% palladium. Drying was then performed under nitrogen at 110° C. The finished heterogeneous catalyst contained 25 g of Pd and 30 g of Mn per litre, each calculated as metal.

b) Surface-modification of a titanium dioxide extrudate with rhodium and manganese:

200 ml of titanium dioxide extrudate were impregnated with 58.4 ml of solution of 21.6 g of manganese(II) chloride in water. Drying was then performed under nitrogen at 110° C. The manganese-doped support was impregnated with 58 ml of solution containing 12.94 g of rhodium(III) chloride hydrate. Drying was then performed under nitrogen at 110° C. The heterogeneous catalyst contained 25 g of rhodium and 30 g of Mn per litre, each calculated as metal.

c) Production of cerium/manganese oxide tablets and surface-modification with palladium:

890 g of sodium hydroxide dissolved in 6 l of water were added at 85° C. to a solution of 997.1 g of cerium(III) chloride 7 hydrate (2.68 mol) and 1351 g of manganese(II) chloride 4 hydrate (6.8 mol) in 17.5 l of water. The precipitate was suction filtered, washed, dried at 110° C. and heat treated for 6 hours at 300° C. The ground support was mixed with 4% of graphite and pressed into tablets.

200 ml of cerium/manganese oxide tablets were impregnated with 72.5 ml of aqueous solution of 33.3 g of sodium tetrachloropalladate(II) solution containing 15% palladium. Drying was then performed in air at 110° C. The heterogeneous catalyst contained 25 g of Pd per litre, calculated as metal.

d) Production of extrudates from a pulverulent rare earth oxide mixture and surface-modification with palladium:

A commercially available mixture of rare earth oxides (Rhône-Poulenc) was worked to a paste with water, extruded, dried for 5 hours at 110° C. and calcined for 5 hours at 400° C. 200 ml of rare earth oxide extrudate were impregnated with 70 ml of aqueous solution of 33.3 g of sodium tetrachloropalladate(II) solution containing 15% palladium. Drying was then performed in air at 110° C. The heterogeneous catalyst contained 25 g of Pd per liter, calculated as metal.

Example 3

Use of supported catalysts for the production of diphenyl carbonate:

a) Use of supported catalyst from Example 1a:

In a test plant, as shown schematically in FIG. 1, a phenolic solution of the components of the reaction system (0.3 wt. % of sodium phenolate, 1.5 wt. % of tetrabutylammonium bromide and 550 ppm of manganese(II) acetylacetonate) was continuously introduced via line 1 into reactor A (1 liter autoclave with sparging agitator, condenser and down-stream cold trap). The reactor filling level was controlled by means of a barometric discharge. 1 g of a supported catalyst produced according to Example 1a was suspended in the reactor. A sintered filter was incorporated in the bottom of the reactor, such that the supported catalyst remained in the reactor during continuous discharge of the reaction product. A pressure of 10 bar was then established by introducing a gas mixture of carbon monoxide and oxygen (95:5 vol. %) via lines 5 and 9. The quantity of gas mixture was set at 300 Nl/h. The reaction mixture was continuously discharged through line 4 and analysed hourly by gas chromatography. Analysis revealed that the reaction mixture contained 9.6% of diphenyl carbonate after 1 hour, 9.5% of diphenyl carbonate after 2 hours and 9.5% of diphenyl carbonate after 3 hours.

b) Use of the supported catalyst from Example 1d:

The same method was used as in Example 3a, but 4 g of a supported catalyst produced according to Example 1d were suspended in the reactor. Analysis of the continuously discharged reaction mixture revealed that the reaction mixture contained 10.9% of diphenyl carbonate after 1 hour, 10.5% of diphenyl carbonate after 2 hours and 10.5% of diphenyl carbonate after 3 hours.

Example 4

Working up the continuously discharged reaction stream

A pump conveyed 500 g/h of a phenolic solution containing 0.3 wt. % of sodium phenolate, 1.5 wt. % of tetrabutylammonium bromide and 1.07 g of manganese(III) acetylacetonate into reactor A via line (1) in FIG. 1. 5 g of the catalyst used in Example 3b were suspended in the reactor.

The temperature of the reaction solution was 80° C. 300 Nl/h of gas mixture consisting of carbon monoxide and oxygen (96.5:3.5 vol. %) passed into the reactor via lines 5 and 9. Reactor pressure was 10 bar and the internal temperature was adjusted to 80° C. Excess reaction gas left the reactor via line 8.

Approximately 500 g/h of reaction solution were discharged from the reactor via line 4 and passed for working up. After approximately 5 hours, the apparatus had reached equilibrium. Gas chromatographic analysis of the hourly samples taken from the discharged reaction mixture revealed a content of 10.2% of diphenyl carbonate. Phenol selectivity was >99%.

The greatest part of the phenol was first removed from the reaction solution by distillation at 120° C. and 5 mbar and concentrated to a DPC content of 80% according to GC.

DPC was isolated by fractionated melt crystallisation in a tubular crystalliser in accordance with EP-A 687 666.

500 g of the previously concentrated reaction solution were introduced into a vertical, jacketed tube 100 cm in height having an internal diameter of approximately 3 cm and cooled from 65° C. at a rate of 2° C./h. At 58° C., the melt was seeded with a few crystals of diphenyl carbonate. When the melt reached 50° C., it was drained out and the heating medium was reheated at 2° C. Once a temperature of 72° C. had been reached, the crystalline mass remaining in the tube was melted and collected separately. It contained 98 wt. % of DPC. The previously separated melt amounting to approximately 260 g in total consisted of 56.5 wt. % (GC) of diphenyl carbonate. The remaining phenol was then removed from the crystallisate by distillation.

The separated mother liquor was combined with the distilled phenol, a further 207 g of phenol were added and reintroduced into the reactor. The feed solution contained approximately 0.2% of DPC according to GC. The reaction solution discharged at equilibrium contained 12.5% of DPC.

The reaction solution could thus be recycled without discernible deactivation.

We claim:

1. A process for the continuous production of diaryl carbonates of the formula

$$R^1-O-CO-O-R^1 \qquad (I)$$

by reacting aromatic hydroxy compounds of the formula

$$R^1-OH \qquad (II),$$

wherein in the formulae $R^1$ means unsubstituted or substituted $C_6-C_{15}$ aryl with carbon monoxide and oxygen at 30°–200° C. and at 1–120 bar, in the presence of a platinum group metal or a compound of a platinum group metal as the catalyst, a co-catalyst, a quaternary salt and a base, wherein the catalyst is used as a supported catalyst in a stationary arrangement or in the fluid phase and the reaction is performed in the condensed phase, and wherein the co-catalyst is attached to a support together with the catalyst.

2. The process of claim 1, wherein the platinum group metal of the supported catalyst is Pt, Ir, Pd, Ru or Rh or two or more thereof, in a quantity of 0.01 to 15 wt. %, calculated as metal and relative to the entire weight of the catalyst.

3. The process of claim 1, wherein carbon, element oxides, element carbides or element salts are used as the support.

4. The process of claim 1, wherein a compound of a metal of groups IB, IIB, IIIA, IVA, IVB, VB, VIB, VIIB, of the iron group or of the group of rare earth metals of Mendeleyev's periodic system of the elements in a quantity of 0 to 20 wt. %, relative to the entire reaction mixture, is used as the co-catalyst.

5. The process of claim 1, wherein one or more salts from the group of ammonium and phosphonium salts, the organic residues of which are identical or different and may mean $C_6$ to $C_{10}$ aryl, $C_7$ to $C_{10}$ aralkyl and $C_1$ to $C_{20}$ alkyl and which contain a halide, tetrafluoroborate or hexafluorophosphate as an anion in a quantity of 0.1 to 50 wt. %, relative to the weight of the reaction mixture, is (are) used as the quaternary salt.

6. The process of claim 1, wherein a hydroxide, carbonate, $C_2$–$C_{12}$ carboxylate or salt of a weak acid or a phenolate of an alkali metal, a tertiary amine or a pyridine base in a quantity of 0.01 to 20 wt. %, relative to the entire reaction mixture, is used as the base.

7. The process of claim 1, wherein CO and $O_2$ are used in a molar ratio of 1:0.001–1 and in a total quantity of 1–100000 Nl per litre of reaction mixture.

8. The process of claim 1, wherein the supported catalyst is used in suspended form in a quantity of 0.001 to 50 wt. %, relative to the introduced aromatic hydroxy compound, or in the form of a fixed bed catalyst with a loading of 0.01 to 20 g of aromatic hydroxy compound per gram of supported catalyst per hour.

9. The process of claim 1, wherein it is performed at 30° to 150° C. and 2 to 80 bar.

* * * * *